US007378444B2

(12) United States Patent
Goodman et al.

(10) Patent No.: US 7,378,444 B2
(45) Date of Patent: May 27, 2008

(54) ANALOGUES OF LIPID MEDIATORS DERIVED FROM OMEGA-3 PUFAS AND METHODS OF USE

(75) Inventors: Daniel W. Goodman, Riverside, CT (US); Michael R. Hanley, Corte Madera, CA (US); Stuart L. Bursten, Napa, CA (US); Charles N. Serhan, Needham, MA (US)

(73) Assignees: Brigham and Women's Hospital, Inc., Boston, MA (US); Resolvyx Pharmaceuticals, Inc., Bedford, MA (US)

( * ) Notice: Subject to any disclaimer, the term of this patent is extended or adjusted under 35 U.S.C. 154(b) by 404 days.

(21) Appl. No.: 10/460,913

(22) Filed: Jun. 13, 2003

(65) Prior Publication Data

US 2004/0044050 A1 Mar. 4, 2004

Related U.S. Application Data

(60) Provisional application No. 60/389,622, filed on Jun. 17, 2002.

(51) Int. Cl.
*A61K 31/22* (2006.01)
*A61K 31/20* (2006.01)
*A61K 31/16* (2006.01)
*C07C 231/00* (2006.01)
*C07C 59/00* (2006.01)

(52) U.S. Cl. .................. 514/549; 514/560; 514/625; 554/61; 554/219

(58) Field of Classification Search ................ 514/549, 514/560, 459, 625; 554/61, 219
See application file for complete search history.

(56) References Cited

U.S. PATENT DOCUMENTS

| 5,411,951 | A | 5/1995 | Mitchell | 514/13 |
| 5,441,951 | A | 8/1995 | Serhan | 514/213 |
| 2002/0055538 | A1* | 5/2002 | Serhan et al. | 514/549 |
| 2003/0191184 | A1 | 10/2003 | Serhan et al. | |
| 2003/0236423 | A1 | 12/2003 | Petasis | |
| 2004/0019110 | A1 | 1/2004 | Van Dyke et al. | |

FOREIGN PATENT DOCUMENTS

| WO | WO 00/55109 | 9/2000 |
| WO | WO 01/60778 A2 | 8/2001 |
| WO | WO 01/70664 A2 | 9/2001 |
| WO | WO 03/053423 A2 | 7/2003 |
| WO | WO 03/084305 A2 | 10/2003 |

OTHER PUBLICATIONS

Serhan et al, Novel functional sets of lipid-derived mediators, Oct. 2000, Rockfeller University press, 192(8), p. 1197-1204.*
Iigo et al. (1997), "Inhibitory Effects of Docosahexaenoic Acid on Colon Carcinoma 26 Metastasis to the Lung", *Br. J. Cancer*, 75:650.
Billman et al., "Prevention of Sudden Cardiac Death by Dietary Pure Omega-3 Polyunsaturated Fatty Acids in Dogs" (1999), *Circulation*, 99:2452.
Simopoulous, et al, "Workshop on the Essentiality of and Recommended Dietary Intakes for Omega-6 and Omega-3 Fatty Acids"(1999), *J. Am. Coll. Nutr.*, 18:487.
Marchioloi et al. "Dietary Supplementation with n-3 Polyunsaturated Fatty Acids and Vitamin E After Myocardial Infarction: Results of the GISSI-Prevenzione Trial" (1999), *Lancet*, 354:447.
Weissmann, G. "Aspirin" (1991), *Sci, Am.*, 264:84.
Marcus, A.J. (1999), "Platelets: Their Roll in Hemostasis, Thrombosis, and Inflammation" *Inflammation: Basic Principles and Clinical Correlates*, J.I. Gallin and R. Snyderman, Editors, Lippincott Williams & Wilkins, Philadelphia, pp. 77-79.
Cláría, J. et al. "Aspirin Triggers Previously Undescribed Bioactive Eicosanoids by Human Endothelial Cell-Leukocyte Interactions" (1995), *Proc. Natl. Acad. Sci USA*, 92:9475.
Serhan et al. "Design of Lipoxin $A_4$ Stable Analogs That Block Transmigration and Adhesion of Human Neutrophils" (1995), *Biochemistry*, 34:14609.
Chiang et al. "Leukotriene $B_4$ Receptor Transgenic Mice Reveal Novel Protective Roles for Lipoxins and Aspirin-Triggered Lipoxins in Reperfusion" (1999), *J. Clin. Invest.* 104:309.
Chiang et al. "Aspirin-Triggered 15-epi-Lipoxin $A_4$ (ATL) Generation by Human Leukocytes and Murione Peritonitis Exudates: Development of a Specific 15-epi-$LXA_4$ ELISA [1]" (1998), *J. Pharmacol. Exp. Ther.*, 287:779.
Xiao et al. "Analysis of Hydroperoxide-Induced Tyrosyl Radicals and Lipoxygenase Activity in Aspirin-Treated Human Prostaglandin H Synthase-2" (1997), Biochemistry, 36:1836.
Clish et al. "Local and Systemic Delivery of a Stable Aspirin-Triggered Lipoxin Prevents Neutrophil Recruitment in vivo" (1999), *Proc. Natl. Acad. Sci USA*, 96:8247.
Serhan et al. "Novel Functional Sets of Lipid-Derived Mediators with Antiinflammatory Actions Generated from Omega-3 Fatty Acids via Cyclooxygenase 2-Nonsteroidal Antiinflammatory Drugs and Transcellular Processing" (2000), *J. Exp. Med.*, 192:1197.
Cronstein et al. "A Mechanism For the Antiinflammatory Effects of Corticosteroids: The Glucocorticoid Receptor Regulates Leukocyte Adhesion to Endothelial Cells and Expression of Endothelial-Leukocyte Adhesion Molecule 1 and Intercellular Adhesion Molecule 1" (1992), *Proc. Natl. Acad. Sci USA*, 89:9991.

(Continued)

*Primary Examiner*—Taylor Victor Oh
(74) *Attorney, Agent, or Firm*—Ropes & Gray LLP

(57) ABSTRACT

The present invention is directed to compounds that are analogues of lipid mediators derived from a fish oil-derived fatty acid, eicosapentaenoic acid [C20:5 ω-3; EPA], but with a longer tissue half-life and enhanced bioactivity. These analogues may be used to treat inflammatory, angioproliferative, cardiovascular, thrombophlebotic, vascular, ocular, dermatologic, neurodegenerative, pulmonary, endocrine, reproductive, rheumatologic and gastrointestinal diseases.

9 Claims, No Drawings

OTHER PUBLICATIONS

Webber et al. The Total Synthesis of the Lipoxins and Related Compounds (1988), *Adv. Exp. Med. Biol.*, 229:61.

Radüchel, B., et al. "Prostagladin Analogs" (1985), *Adv. Prost. Thromb. Leuko. Res.*, 14:263.

Kobayashi, Y. et al "Highly Stereocontrolled Total Synthesis of Leukotriene $B_4$ 20-Hydroxyleukotriene $B_4$ Leukotriene $B_3$ and Their Analogues" (1990), *J. Org. Chem.*, 55:5324.

Nicolaou, K.C. et al. "Lipoxins and Related Eicosanoids: Biosynthesis, Biological Properties, and Chemical Synthesis" (1991), *Agnew Chem. Int. Ed. Engl.*, 30:1100.

Serhan, C. et al. "High-Performance Liquid Chromatography Separation and Determination of Lipoxins" (1990), *Meth. Enzymol.*, 187:167.

Minto, C.F. et al., "Pharmacokinetics and Pharmacodynamics of Nandrolone Esters in Oil Vehicle: Effects of Ester, Injection Site and Injection Volume[1]" (1997), *J. Pharmacol. Exp. Ther.*, 281:93.

Rohatagi et al. "Pharmacokinetic and Pharmacodynamic Evaluation of Triamcinolone Acetonide After Intravenous, Oral, and Inhaled Administration" (1995), *J. Clin. Pharmacol.*, 35:1187.

Tjwa, Martin K.T. "Budesonide Inhaled via Turbuhaler: A More Effective Treatement for Asthma Than Beclomethasone Dipropionate Via Rotahaler" (1995), *Ann. Allergy Asthma & Immunol.*, 75:107.

Rao, K.P. "Recent Developments of Collagen-Based Mterials for Medical Applications and Drug Delivery Systems" (1995), *J. Biomater Sci. Polym. Edn*, 7:623.

Gao, Z. et al. "Controlled Release of a Contraceptive Steroid from Biodegradable and Injectable Gel Formulations: In Vitro Evaluation" (1995), *Pharm. Res.*, 12:857.

Eyles et al. "Oral Delivery and Fate of Poly(lactic Acid) Microsphere-Encapsulated Interferon in Rats" (1997),*J. Pharm. Pharmacol.*, 49:669.

Al-Muhammed et al. "In-Vivo Studies on Dexamethasone Sodium Phosphate Liposomes" (1996), *J. Microencapsul.*, 13:293.

Ostro, M.J. et al. "Use of Liposomes as Injectable-Drug Delivery Systems" (1989), *Am. J. Hosp. Pharm.*, 46:1576.

Shimazaki et al., "12 (R)-Methyl-Leukotriene $B_3$: A Stable Leukotriene B Analogue Toward the Reductase Metabolism" (1993), *Prostaglandins*, 45:335.

Kobayashi et al., "Highly Stereocontrolled, Multigram Scale Synthesis of Leukotriene $B_4$" (1987), *Tetrahedron Lett.*, 38:5849.

Clissold D. "The Potential For Prostaglandin Pharmaceuticals" (1999), Lipids in Health and Nutrition, J.H.P. Tyman editor, Royal Society of Chemistry, Cambridge UK, pp. 115-129.

Serhan et al., "Unorthodox Routes to Prostanoid Formation: New Twists in Cyclooxygenase-Initiated Pathways" (2001), *J. Clin. Invest.*, 107:1481.

Serhan et al., "Resolvins: A Family of Bioactive Products of Omega-3 Fatty Acid Transformation Circuits Initiated by Aspirin Treatment that Counter Proinflammation Signals" (2002), *J. Exp. Med.*, 196:1025.

Serhan et al., "Lipid-Derived Mediators in Endogenous Anit-Inflammation and Resolution: Lipoxins and Asiprin-Triggered 15-epi-Lipoxins" (2002), *TheScientificWorldJOURNAL*, 2:169.

Clish et al., "Oxidoreductases In Lipoxin $A_4$ Metabolic Inactivation" (2000), *J. Bio Chem.*, 275:25372.

Takano et al., "Aspirin-Triggered 15-Epi-Lipoxin $A_4$ ($LXA_4$) and $LXA_4$ Stable Analogues Are Potent Inhibitors of Acute Inflammation: Evidence for Anti-Inflammatory Receptors" (1997), *J. Exp. Med.*, 185:1693.

Konno et al., "Synthesis of Structural Analogues of Leukotriene $B_4$ and their Receptor Binding Activity" (1997), *Biorg. & Med. Chem.*, 4:1621.

Serhan et al., "Anit-Microinflammatory Lipid Signals Generated from Dietary N-3 Fatty Acids Via Cyclooxygenase-2 and Transcellular Processing: A Novel Mechanism for Nsaid and N-3 PUFA Therapeutic Actions" (2000), *J. Physiol. Pharmacol.* 51:643:54.

* cited by examiner

ANALOGUES OF LIPID MEDIATORS DERIVED FROM OMEGA-3 PUFAS AND METHODS OF USE

CROSS REFERENCE TO RELATED APPLICATIONS

This application is entitled to the benefit of and claims priority from U.S. Provisional Patent Application No. 60/389,622, filed Jun. 17, 2002, which is hereby incorporated by reference.

FIELD OF THE INVENTION

The present invention is directed to compounds that are analogues of lipid mediators derived from a fish oil-derived fatty acid, eicosapentaenoic acid, but with a longer tissue half-life and enhanced bioactivity. These analogues may be used to treat inflammatory, angioproliferative, cardiovascular, thrombophlebotic, vascular, ocular, dermatologic, neurodegenerative, pulmonary, endocrine, reproductive, rheumatologic or gastrointestinal diseases.

BACKGROUND OF THE INVENTION

Supplementation of dietary omega-3 polyunsaturated fatty acids ("ω-3 PUFAs") such as eicosapentaenoic acid, a component of fish oils, may have beneficial effects in diseases such as arteriosclerosis, arthritis, asthma and cancer, which may be mediated by antithrombotic, immunoregulatory and anti-inflammatory responses [1, 2, 3]. The potential of ω-3 PUFAs for preventative actions in cardiovascular diseases was recently supported by the finding that major dietary ω-3 PUFAs, such as eicosapentaenoic acid (C20:5 ω-3; EPA) and docosahexaenoic acid (C22:6 ω-3; DHA), have a dramatic effect on ischemia-induced ventricular fibrillation [4]. Emergence of such possible preventative and/or therapeutic actions of ω-3 PUFA supplementation in infant nutrition, cardiovascular diseases, and mental health has led to a call for recommended dietary intakes by an international workshop [5]. The Gruppo Italiano per lo Studio della Sopravvivense nell'Infarto Miocardio (GISSI) Prevenzione trial evaluated the effects of ω-3 PUFA supplementation with 11,300 patients surviving myocardial infarction taking ~1 g of ω-3 PUFA daily (n=2,836) along with recommended preventive treatments including aspirin, and reported a significant benefit with a decrease in cardiovascular death [6]. However, the mechanisms underlying the protective action of dietary ω-3 PUFAs in these studies and other studies including those concerned with diseases of the skin, bowel, and neural tissues are not currently understood. One of the many hypothesized elements of the mechanism(s) of action of ω-3 PUFAs is that naturally occurring metabolites, formed from these PUFAs, may act as mediators that provide important biological functions, but these metabolites are not stable.

Thus, large doses of known ω-3 PUFAs are required for efficacy while at the same time many ω-3 PUFA metabolites have poor in vivo stability as they are rapidly inactivated by diverse metabolic processes. Accordingly, there is a need for new analogues which may be more potent and active than ω-3 PUFAs and which have greater in vivo stability than naturally occurring ω-3 PUFA metabolites. Further, such new analogues may elucidate the protective mechanism(s) associated with ω-3 PUFAs.

SUMMARY OF THE INVENTION

The instant invention satisfies these and other needs by providing analogues of naturally occurring trihydroxy derivatives of EPA where the naturally occurring trihydroxy molecules contain a hydroxyl group at C-18 of the fatty acid chain. The analogues of the current invention have active regions that are the same or similar to the active regions of the naturally occurring trihydroxy derivatives, but metabolic transformation regions which are more resistant to in vivo catabolism. The compounds of the invention therefore retain the biological activity of the naturally occurring, C-18 hydroxy trihydroxy derivatives of EPA, but have longer metabolic half-lives. Many of the instant disclosed analogues also have an increased in vivo potency and/or enhanced bioactivity as compared to the natural C-18 hydroxy trihydroxy derivatives of EPA.

In one aspect, the current invention provides compounds, which are analogues of naturally occurring 5,12,18R-trihydroxyeicosapentanoic acid ("5,12,18R-triHEPE") or olefin isomers thereof. The compounds of the invention have an active region that is the same or similar to 5,12,18R-triHEPE, but a metabolic transformation region which is more resistant to in vivo catabolism. In one preferred embodiment, the present invention provides compounds of structural formula (I):

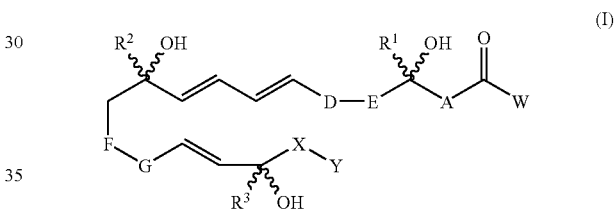

(I)

and pharmaceutically acceptable salts, hydrates and solvates thereof, wherein:

D-E and F-G are independently cis or trans —C=C— or —C≡C—;

$R^1$, $R^2$ and $R^3$ are independently selected from the group consisting of hydrogen, (C1-C4) alkyl, (C1-C4) alkoxy, —CH$_2$R$^4$, —CHR$^4$R$^4$ and —CR$^4$R$^4$R$^4$;

each $R^4$ is independently selected from the group consisting of —CN, —NO$_2$ and halogen;

W is selected from the group consisting of —R$^5$, —OR$^5$, —SR$^5$ and —NR$^5$R$^5$;

each $R^5$ is independently selected from the group consisting of hydrogen, (C1-C6) alkyl optionally substituted with one or more of the same or different R groups, (C5-C14) aryl optionally substituted with one or more of the same or different R groups, phenyl optionally substituted with one or more of the same or different R groups, (C6-C 16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups and a detectable label molecule;

A is selected from the group consisting of (C1-C6) alkylene optionally substituted with 1, 2, 3, 4, 5 or 6 of the same or different halogen atoms, —(CH$_2$)$_m$—O—CH$_2$— and —(CH$_2$)$_m$—S—CH$_2$—, where m is an integer from 0 to 4;

X is selected from the group consisting of —$(CH_2)_n$— and —$(CH_2)_n$—O—, where n is an integer from 0 to 6;

Y is selected from the group consisting of hydrogen, (C1-C6) alkyl optionally substituted with one or more of the same or different R groups, (C5-C14) aryl optionally substituted with one or more of the same or different R groups, phenyl optionally substituted with one or more of the same or different R groups, (C6-C16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups and a detectable label molecule;

each R is independently selected from the group consisting of an electronegative group, =O, —$OR^a$, (C1-C3) haloalkyloxy, =S, —$SR^a$, =$NR^a$, =$NONR^a$, —$NR^cR^c$, halogen, —$CF_3$, —CN, —NC, —OCN, —SCN, —NO, —$NO_2$, =$N_2$, —$N_3$, —$S(O)R^a$, —$S(O)_2R^a$, —$S(O)_2OR^a$, —$S(O)_2NR^cR^c$, —$OS(O)R^a$, —$OS(O)_2R^a$, —$OS(O)_2OR^a$, —$OS(O)_2NR^cR^c$, —$C(O)R^a$, —$C(O)OR^a$, —$C(O)NR^cR^c$, —$C(NH)NR^cR^c$, —$OC(O)R^a$, —$OC(O)OR^a$, —$OC(O)NR^cR^c$, —$OC(NH)NR^cR^c$, —$NHC(O)R^a$, —$NHC(O)OR^a$, —$NHC(O)NR^cR^c$ and —$NHC(NH)NR^cR^c$;

each $R^a$ is independently selected from the group consisting of hydrogen and (C1-C4) alkyl; and each $R^c$ is independently an $R^a$ or, alternatively, $R^cR^c$ taken together with the nitrogen atom to which it is bonded forms a 5 or 6 membered ring, with the proviso that when X-Y is —$CH_2CH_3$, then at least one of $R^1$, $R^2$ or $R^3$ is other than hydrogen.

In another aspect, the present invention provides pharmaceutical compositions comprising one or more compounds of the invention, with or without other active pharmaceutical ingredients, in admixture with a pharmaceutically acceptable vehicle. Such a preparation can be administered according to the methods of the current invention.

In yet another aspect, the present invention is drawn to methods for treating or preventing inflammation or inflammatory disease in a mammal. The method involves administering a prophylactically or therapeutically effective amount of at least one compound of the invention, or a pharmaceutical composition thereof.

Additional features and advantages of the invention will become more apparent from the following detailed description and claims.

DETAILED DESCRIPTION OF THE INVENTION

Definitions

As used herein, the following terms shall have the following meanings:

"Compounds of the invention" refers to trihydroxy eicosapentaenoic acid analogues of a natural 5,12,18R-triHEPE and compounds encompassed by generic formulae disclosed herein and includes any specific compounds within those formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$.

"Biological activity" and its contextual equivalents "activity" and "bioactivity" means that a compound elicits a statistically valid effect in any one biological test assays. Preferably, the threshold for defining an "active" compound will be reproducible and statistically valid effects of at least 25% deviation from untreated control at concentrations at or lower than 1 μM.

"Biological test assay" means a specific experimental procedure. Non-limiting examples of biological test assays include: 1) ligand binding, either direct or indirect, to a purified target, subcellular fraction, intact cell, or cell or tissue extract; 2) metabolic protection with enhanced half-life when exposed to a purified target, subcellular fraction, intact cell, cell or tissue extract, or administered to intact organism by any route; 3) prevention, reversal, or amelioration of cell- and tissue-based functional responses recognized by skilled artisans to represent surrogates for anti-inflammatory action (e.g., altered cytokine production and release); and 4) prevention, reversal, or amelioration of symptoms and/or disease processes in animal models of inflammation and inflammatory disease.

"Detectable label" means any chemical or biological modality which can be used to track, trace, localize, quantify, immobilize, purify, or identify compounds through appropriate means of detection known in the art. Non-limiting examples of detectable labels include fluorescence, phosphorescence, luminescence, radioactive or biospecific affinity capture labels.

"Electronegative group" is a chemical group that tends to acquire rather than lose electrons in its chemical interactions. Examples of electronegative groups include, but are not limited to, —$NO_2$, ammonium salts, sulfonyl groups, carbonyl groups, halogens, esters, carboxylic acids, nitriles, etc.

"Trihydroxy eicosapentaenoic acid analogues" means a compound which has an "active region" that functions like the active region of a "natural trihydroxy derivative of eicosapentaenoic acid", but which has a "metabolic transformation region" that differs from the natural trihydroxy derivative of eicosapentaenoic acid. Such compounds include compounds which are structurally similar to a natural trihydroxy derivative of eicosapentaenoic acid, compounds which share the same receptor recognition site as a trihydroxy derivative of eicosapentaenoic acid, compounds which share the same or similar metabolic transformation regions as a natural trihydroxy derivative of eicosapentaenoic acid and compounds which are recognized in the art as being analogues of a natural trihydroxy derivative of eicosapentaenoic acid. Trihydroxy eicosapentaenoic acid analogues include trihydroxy eicosapentaenoic acid analogue metabolites.

"In Situ" refers to and includes the terms "in vivo," "ex vivo" and "in vitro" as these terms are commonly recognized and understood by the skilled artisan. Moreover, the phrase "in situ" is employed herein in its broadest connotative and denotative context to identify an entity, cell, or tissue as found or in place, without regard to its source or origin, its condition or status or its duration or longevity at that location or position.

"Natural tri-hydroxy derivative of eicosapentaenoic acid" means a compound that is generated in situ from eicosapentaenoic acid and that contains three hydroxyl groups.

"5,12,18-tri-HEPE" means a natural trihydroxy derivative of eicosapentaenoic acid possessing hydroxyl groups at carbons 5, 12, and 18.

"Active region" means the region of a natural trihydroxy derivative of eicosapentaenoic acid or of a trihydroxy eicosapentaenoic acid analogue, which is associated with in vivo cellular interactions. The active region may bind to the recognition site of a cellular receptor for a natural trihydroxy derivative of eicosapentaenoic acid or a macromolecule or complex of macromolecules, including an enzyme and its cofactor. In one embodiment, trihydroxy eicosapentaenoic acid analogues have an active region comprising C5-C18 of 5S,12R,18R-trihydroxy-6,14-cis-8,10,16-trans eicosapentaenoic acid.

"Metabolic transformation region" means that portion of a natural trihydroxy derivative of eicosapentaenoic acid, a metabolite of a natural trihydroxy derivative of eicosapentaenoic acid, or a trihydroxy eicosapentaenoic acid analogue including a metabolite of a trihydroxy eicosapentaenoic acid analogue, upon which an enzyme or an enzyme and its cofactor may perform one or more metabolic transformations, which that enzyme or enzyme and cofactor normally performs on natural trihydroxy derivative of eicosapentaenoic acid. The metabolic transformation region may or may not be susceptible to the transformation. Non-limiting examples of metabolic transformation regions of a natural trihydroxy derivative of eicosapentaenoic acid include portions of 5S,12R,18R-trihydroxy-6,14-cis-8,10,16-trans eicosapentaenoic acid such as: 1) the terminal regions of the molecule (i.e., the carboxyl terminus including the carboxyl group and immediately adjacent alkyl moiety, which may be metabolized via a process of β-oxidation followed by cleavage of the carboxyl group, or the ω-terminal which may also be oxidized), 2) the C-18-CHOH— group which may be metabolized via oxidation, 3) the C10-C11 or C16-C17 trans double bonds which may be metabolized via reduction to single bond(s), 4) the C5 or C12 CHOH groups which may be metabolized via oxidation, 5) the C6-C7 or C14-C15 cis double bonds which may be metabolized via isomerization to trans double bonds, 6) or some combination of these portions. In broader terms, non-limiting examples of metabolic transformation regions of natural trihydroxy derivatives of eicosapentaenoic acid include: 1) the β-terminus, 2) the ω-terminus, 3) CHOH groups, 4) trans double bonds adjacent to CHOH groups and 5) cis double bonds.

"Inhibits metabolism" means the blocking or reduction of activity of an enzyme which metabolizes a natural trihydroxy derivative of eicosapentaenoic acid. The blockage or reduction may occur by covalent bonding, by irreversible binding, by reversible binding which has a practical effect of irreversible binding, or by any other means which prevents the enzyme from operating in its usual manner on another trihydroxy eicosapentaenoic acid analogue, including a trihydroxy eicosapentaenoic acid analogue metabolite, a natural trihydroxy derivative of eicosapentaenoic acid, or a metabolite of a natural trihydroxy derivative of eicosapentaenoic acid.

"Resists metabolism" means failing to undergo one or more of the metabolic degradative transformations by at least one of the enzymes which metabolize natural trihydroxy derivatives of eicosapentaenoic acid. Non-limiting examples of trihydroxy eicosapentaenoic acid analogues that resists metabolism are: 1) a structure which is not susceptible to β-oxidation as may be obtained via modifications of the carboxyl group or the alkyl moiety immediately adjacent to the alkyl group, 2) a structure which is not susceptible to ω-oxidation which may be obtained via replacement of the ω-terminus with an appropriate group; 3) a structure which resists conversion of a cis double bond to a trans double bond, which may for example be obtained by replacing the cis double bond with a triple bond, and 4) a structure which can not be oxidized to the 18-oxo form or in general where one or more CHOH groups are resistant to oxidation which may for example be obtained by placing another substituent such as a methyl group at the relevant carbon (e.g., at C18 if to resist 18-oxo formation). Modifying the C18 carbon such as by substitution with a methyl group also protects the adjacent trans double bond from reduction.

"More slowly undergoes metabolism" means having slower reaction kinetics, or requiring more time for the completion of the series of metabolic transformations by one or more of the enzymes which metabolize natural trihydroxy derivatives of eicosapentaenoic acid. A non-limiting example of a trihydroxy eicosapentaenoic acid analogue which more slowly undergoes metabolism is a structure which has a higher transition state energy for C-18 dehydrogenation than does 5S,12R,18R-trihydroxy-6,14-cis-8,10,16-trans eicosapentaenoic acid because the analogue is sterically hindered at C-19.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) salts formed when an basic proton is present in the parent compound such as acid addition salts, formed with inorganic acids such as hydrochloric acid, hydrobromic acid, sulfuric acid, nitric acid, phosphoric acid, and the like; or those formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton is present in the parent compound and either is replaced by a metal ion, e.g., an alkali metal ion, an alkaline earth ion, or an aluminum ion; or coordinates with an organic base such as ethanolamine, diethanolamine, triethanolamine, N-methylglucamine, triethylamine, propylamino, diazabicycloundecane and the like.

"Pharmaceutically acceptable vehicle" refers to a diluent, adjuvant, excipient or carrier with which a compound of the invention is administered.

"Prodrug" refers to a derivative of a drug molecule that requires a transformation within the body to release the active drug. Prodrugs are frequently (though not necessarily) pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, imine, phosphonyl, phosphoryl or sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which contain different functional groups other than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated (e.g., methyl and ethyl esters, acetate or propionate groups or glycol esters) or alkylated such as benzyl, and trityl ethers as well as alkyl ethers, tetrahydropyranyl ethers, trialkylsilyl ethers (e.g., TMS or TIPPS groups) and allyl ethers.

"Subject" means living organisms susceptible to conditions or diseases caused or contributed to by inflammation, inflammatory responses, vasoconstriction and myeloid suppression. Examples of subjects include humans, dogs, cats, cows, goats and mice. The term subject is further intended to include transgenic species such as, for example, transgenic mice.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cyclo-prop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In a preferred embodiment, an alkyl group is (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In a preferred embodiment, the alkanyl group is (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In a preferred embodiment, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In a preferred embodiment, the alkynyl group is (C2-C6) alkynyl.

"Alkdiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkdiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1- diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In a preferred embodiment, the alkdiyl group is (C1-C6) alkdiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain or branched alkdiyl group having two terminal monovalent radical centers derived by the removal of one hydrogen atom from each of the two terminal carbon atoms of straight-chain parent alkane, alkene or alkyne. Typical alkylene groups include, but are not limited to, methylene (methano); ethylenes such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Heteroalkyl," "Heteroalkanyl," "Heteroalkenyl," "Heteroalkanyl," "Heteroalkdiyl" and "Heteroalkylene" by themselves or as part of another substituent refer to alkyl, alkanyl, alkenyl, alkynyl, alkdiyl and alkylene groups, respectively, in which one or more of the carbon atoms (and any associated hydrogen atoms) are each independently replaced with the same or different heteratoms or heteroatomic groups. Typical heteratoms and/or heteroatomic groups which can be included in these groups include, but are not limited to, —O—, —S—, —O—O—, —S—S—, —O—S—, —NR'—, =N—N=, —N=N—, —N=N—NR'—, —S(O)—, —S(O)$_2$—, —S(O)$_2$NR'—, and the like, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position where the heterocycloalkyl group is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical hetercycloalkyl groups include, but are not limited to, tetrahydrofurnyl (e.g., tetrahydrofuran-2-yl, tetrahydrofuan-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl" by itself or as part of another substituent refers to a monovalent aromatic hydrocarbon group having the stated number of carbon atoms (i.e., C5-C14 means from 5 to 14 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. Preferably, the aryl group is (C5-C14) aryl, more preferably, the aryl group is (C5-C10) aryl. Particularly preferred aryls include cyclopentadienyl, phenyl and naphthyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In a preferred embodiment, the arylalkyl group is (C6-C20) arylalkyl, e.g., the alkanyl, alkenyl or alkynyl moiety of the arylalkyl group is (C1-C6) and the aryl moiety is (C5-C14). In a particularly preferred embodiment the arylalkyl group is (C6-C13), e.g., the alkanyl, alkenyl or alkynyl moiety of the arylalkyl group is (C1-C3) and the aryl moiety is (C5-C10).

"Arylheteroalkyl" by itself or as part of another substituent refers to an acyclic heteroalkyl group in which one of the hydrogen atoms bonded to a carbon or heteroatom, typically a terminal carbon or heteroatom, is replaced with an aryl group. Where arylheteroalkyl moieties are intended to have specified levels of saturation, the nomenclature aryl heteroalkanyl, aryl heteroalkenyl and/or aryl heteroalkynyl is used. In a preferred embodiment, the arylheteroalkyl group is a 6-26 membered arylheteroalkyl, e.g., the heteroalkyl moiety is 1-6 membered and the aryl moiety is (C5-C20) aryl. In a particularly preferred embodiment, the arylheteroalkyl group is 6-13 membered, e.g., the heteroalkyl moiety is 1-3 membered and the aryl moiety is (C5-C10).

"Parent Heteroaromatic Ring System" refers to a parent aromatic ring system in which one or more carbon atoms (and any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, arsindole, benzodioxan, benzofuran, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In a preferred embodiment, the heteroaryl group is a 5-14 membered heteroaryl, with 5-10 membered heteroaryl being particularly preferred. The most preferred heteroaryl groups are those derived from thiophene, pyrrole, benzothiophene, benzodioxan, benzofuran, indole, pyridine, quinoline, imidazole, oxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In a preferred embodiment, the heteroarylalkyl group is a 6-20 membered heteroarylalkyl, e.g., the alkanyl, alkenyl or alkynyl moiety of the heteroarylalkyl is (C1-C6) alkyl and the heteroaryl moiety is a 5-14-membered heteroaryl. In a particularly preferred embodiment, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent refer to fluorine, chlorine, bromine and iodine, or fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyl, etc. up to perhaloalkyls. For example, the expression "(C1-C2) haloalkyl" includes 1-fluoromethyl, difluoromethyl, tri fluoromethyl, 1-fluoroethyl, 1,1-difluoroethyl, 1,1,1-trifluoroethyl, perfluoroethyl, etc.

The Compounds of the Invention

The instant invention is based on the observation that natural trihydroxy derivatives of eicosapentaenoic acid, where the natural compound contains a C-18 hydroxyl group, are rapidly metabolized by a large variety of different enzymes in vivo in a wide range of highly specific metabolic transformations. Among lipid signals derived from PUFAs, some such signals (e.g., leukotrienes) are recognized by the skilled artisan to be metabolized in vivo primarily by ω-oxidation followed by β-oxidation. Other signals (e.g., lipoxins) are metabolized primarily by other routes such as a series of oxidation and reduction reactions, which act on certain hydroxyl sites and adjacent double bonds of the lipoxin molecule. For example, LXA$_4$ metabolism occurs, at least in part, via oxidation of the C-15 hydroxyl to generate 15-oxo-LXA$_4$, reduction of the C-13,14 double bond to yield 13,14-dihydro-15-oxo-LXA$_4$ and further reduction to yield 13,14-dihydro-LXA$_4$.

Accordingly, the compounds of the invention include trihydroxy eicosapentaenoic acid analogues, which have the activity of natural trihydroxy derivatives of eicosapentaenoic acid, that contain a C-18 hydroxyl group, but which are more resistant to metabolic degradation in vivo. The C-1 to C-17 portion of natural trihydroxy derivatives of eicosapentaenoic acid, which contain a C-18 hydroxyl group, may or may not be conserved in the compounds of the invention. It should also be understood that the compounds of the invention may include different substitutions on the fatty acid side chain. Similarly, the C19-C20 terminal of the compounds of the invention may or may not be substituted.

In one embodiment, the compounds of the invention are trihydroxy eicosapentaenoic acid analogues of a natural 5,12,18R-triHEPE. In a preferred embodiment, the present invention includes compounds of structural formula (I):

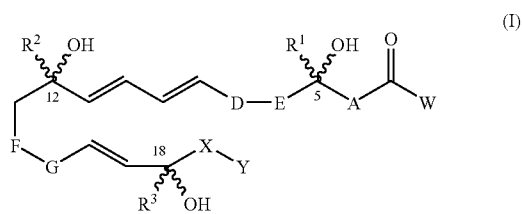

and pharmaceutically acceptable salts, hydrates and solvates thereof, wherein:

D-E and F-G are independently are cis or trans —C═C— or —C≡C—;

R$^1$, R$^2$ and R$^3$ are independently selected from the group consisting of hydrogen, (C1-C4) straight-chained or branched alkyl, (C1-C4) alkoxy, —CH$_2$R$^4$, —CHR$^4$R$^4$ and —CR$^4$R$^4$R$^4$;

each R$^4$ is independently selected from the group consisting of CN, —NO$_2$ and halogen;

W is selected from the group consisting of —R$^5$, —OR$^5$, —SR$^5$ and —NR$^5$R$^5$;

each R$^5$ is independently selected from the group consisting of hydrogen, (C1-C6) alkyl optionally substituted with one or more of the same or different R groups, (C5-C 14) aryl optionally substituted with one or more of the same or different R groups, phenyl optionally substituted with one or more of the same or different R groups, (C6-C16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups and a detectable label molecule;

A is selected from the group consisting of (C1-C6) alkylene optionally substituted with 1, 2, 3, 4, 5 or 6 of the same or different halogen atoms, —(CH$_2$)$_m$—O—CH$_2$— and —(CH$_2$)$_m$—S—CH$_2$—, where m is an integer from 0 to 4;

X is selected from the group consisting of —(CH$_2$)$_n$— and —(CH$_2$)$_n$—O—, where n is an integer from 0 to 6;

Y is selected from the group consisting of hydrogen, (C1-C6) alkyl optionally substituted with one or more of the same or different R groups, (C5-C14) aryl optionally substituted with one or more of the same or different R groups, phenyl, optionally substituted with one or more of the same or different R groups, (C6-C16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups and a detectable label molecule;

each R is independently selected from the group consisting of an electronegative group, =O, —OR$^a$, (C1-C3) haloalkyloxy, =S, —SR$^a$, =NR$^a$, =NONR$^a$, —NR$^c$R$^c$, halogen, —CF$_3$, —CN, —NC, —OCN, —SCN, —NO, —NO$_2$, =N$_2$, —N$_3$, —S(O)R$^a$, —S(O)$_2$R$^a$, —S(O)$_2$OR$^a$, —S(O)$_2$NR$^c$R$^c$, —OS(O)R$^a$, —OS(O)$_2$R$^a$, —OS(O)$_2$OR$^a$, —OS(O)$_2$NR$^c$R$^c$, —C(O)R$^a$, —C(O)OR$^a$, —C(O)NR$^c$R$^c$, —C(NH)NR$^c$R$^c$, —OC(O)R$^a$, —OC(O)OR$^a$, —OC(O)NR$^c$R$^c$, —OC(NH)NR$^c$R$^c$, —NHC(O)R$^a$, —NHC(O)OR$^a$, —NHC(O)NR$^c$R$^c$ and —NHC(NH)NR$^c$R$^c$;

each R$^a$ is independently selected from the group consisting of hydrogen and (C1-C4) alkyl; and each R$^c$ is independently an R$^a$ or, alternatively, R$^c$R$^c$ taken together with the nitrogen atom to which it is bonded forms a 5 or 6 membered ring, with the proviso that when X-Y is —CH$_2$CH$_3$, then at least one of R$^1$, R$^2$ or R$^3$ is other than hydrogen.

In another embodiment, the compounds of the invention include trihydroxy eicosapentaenoic acid analogues of 5S,12R,18R-trihydroxy-6,14-cis-8,10,16-trans-eicosapentaenoic acid.

In still another embodiment, the compounds of the invention do not include 4,11,17-trihydroxy docosahexenoic acid.

In another illustrative embodiment, the present invention provides compounds of structural formula (II):

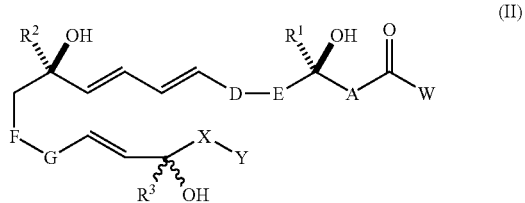

(II)

and pharmaceutically available salts, hydrates and solvates thereof, wherein D-E and F-G, R$^1$, R$^2$, R$^3$, A, W, X and Y are as previously defined, with the proviso that when X-Y is CH$_2$CH$_3$, then at least one of R$^1$, R$^2$ or R$^3$ is other than hydrogen.

In one embodiment of compounds of Formulae (I) and (II), D-E and F-G are both C═C. In another embodiment, D-E is cis C═C— and F-G is trans C═C—. In still another embodiment, D-E and F-G are cis —C═C—. In still another embodiment, D-E is —C≡C— and F-G is C═C—. In still another embodiment, D-E is —C≡C— and F-G is cis C═C—. In still another embodiment, D-E and F-G are —C≡C—.

In one embodiment of compounds of Formulae (I) and (II), R$^1$, R$^2$, R$^3$ are independently hydrogen or (C1-C4) alkyl. In another embodiment, R$^1$, R$^2$, R$^3$ are independently hydrogen or methyl. In one embodiment of compounds of Formulae (I) and (II), R$^1$ is hydrogen. In still another embodiment, R$^1$ is hydrogen and R$^2$ and R$^3$ are independently hydrogen or methyl.

In one embodiment of compounds of Formulae (I) and (II), W is —OR$^5$ and —NR$^5$R$^5$. In another embodiment, W is —OR$^5$ and —NR$^5$R$^5$ and each R$^5$ is independently selected from the group consisting of hydrogen, (C1-C6) alkyl and a detectable label molecule. In still another embodiment, W is —OR$^5$ and R$^5$ is hydrogen, methyl or isopropyl. In still another embodiment, W is —NR$^5$R$^5$ and each R$^5$ is hydrogen or ethyl. In still another embodiment, W is —NHR$^5$ and R$^5$ is ethyl.

In one embodiment of compounds of Formulae (I) and (II), A is (C1-C6) alkylene or —(CH$_2$)$_m$—O—CH$_2$—. Preferably, A is (C2-C3) alkylene or —CH$_2$—O—CH$_2$—.

In one embodiment of compounds of Formulae (I) and (II), X is —(CH$_2$)$_n$—O— or —(CH$_2$)$_n$— and n is 0 or 1. In one embodiment of compounds of Formulae (I) and (II), Y is (C1-C6) alkyl or aryl. Preferably, Y is methyl, phenyl or substituted phenyl.

In one embodiment of compounds of Formula (I) and (II), D-E is —C≡C— and F-G is —C═C—, R$^1$, R$^2$ and R$^3$ are independently hydrogen, (C1-C4) alkyl or CF$_3$, W is —OR$^5$ or —NR$^5$R$^5$ and each R$^5$ is independently hydrogen or (C1-C6) alkyl, A is (C1-C6) alkylene or —(CH$_2$)$_m$—O—CH$_2$—, X is —CH$_2$—O— or —CH$_2$—, or CF$_3$, Y is (C1-C6) alkyl or aryl. In another embodiment of compounds of Formula (I) and (II), D-E is —C≡C— and F-G is cis —C═C—, R$^1$, R$^2$ and R$^3$ are independently hydrogen, (C1-C4) alkyl or CF$_3$, W is —OR$^5$ or —NR$^5$R$^5$ and each R$^5$ is independently hydrogen or (C1-C6) alkyl, A is (C1-C6) alkylene or —(CH$_2$)$_m$—O—CH$_2$—, X is —CH$_2$—O— or —CH$_2$—, or CF$_3$, Y is (C1-C6) alkyl or aryl. In still another embodiment of compounds of Formula (I) and (II), D-E and F-G are both —C═C—, R$^1$, R$^2$ and R$^3$ are independently hydrogen, (C1-C4) alkyl or CF$_3$, W is —OR$^5$ or —NR$^5$R$^5$, A is (C1-C6) alkylene or —(CH$_2$)$_m$—O—CH$_2$—, X is —CH$_2$—O— or —CH$_2$—, Y is (C1-C6) alkyl or aryl. In still another embodiment of compounds of Formula (I) and (II), D-E and F-G are both cis —C═C—, R$^1$, R$^2$ and R$^3$ are independently hydrogen, (C1-C4) alkyl or CF$_3$, W is —OR$^5$ or —NR$^5$R$^5$, A is (C1-C6) alkylene or —(CH$_2$)$_m$—O—CH$_2$—, X is —CH$_2$—O— or —CH$_2$—, Y is (C1-C6) alkyl or aryl. In still another embodiment of compounds of Formula (I) and (II), D-E is cis —C═C—, and F-G is trans-C═C—, R$^1$, R$^2$ and R$^3$ are independently hydrogen, (C1-C4) alkyl or CF$_3$, W is —OR$^5$ or —NR$^5$R$^5$, A is (C1-C6) alkylene or —(CH$_2$)$_m$—O—CH$_2$—, X is —CH$_2$—O— or —CH$_2$—, Y is (C1-C6) alkyl or aryl. In still another embodiment of compounds of Formula (I) and (II), D-E and F-G are both —C≡C—, R$^1$, R$^2$ and R$^3$ are independently hydrogen, (C1-C4) alkyl or CF$_3$, W is —OR$^5$ or —NR$^5$R$^5$, A is (C1-C6) alkylene or —(CH$_2$)$_m$—O—CH$_2$—, X is —CH$_2$—O— or —CH$_2$—, Y is (C1-C6) alkyl or aryl.

In one embodiment of compounds of Formula (I) and (II), D-E is —C≡C— and F-G is —C═C—, R$^1$, R$^2$ and R$^3$ are independently hydrogen or methyl, W is —OR$^5$ or —NR$^5$R$^5$ and each R$^5$ is independently, hydrogen, methyl, ethyl or isopropyl, A is (C2-C3) alkylene or —CH$_2$—O—CH$_2$—, X is —CH$_2$—O— or —CH$_2$—, Y is methyl, phenyl or substituted phenyl. In another embodiment of compounds of Formula (I) and (II), D-E is —C≡C— and F-G is cis —C═C—, R$^1$, R$^2$ and R$^3$ are independently hydrogen or methyl, W is —OR⁵ or —NR⁵R⁵ and each R⁵ is independently, hydrogen, methyl, ethyl or isopropyl, A is (C2-C3) alkylene or —CH₂—O—CH₂—, X is —CH₂—O— or —CH₂—, Y is methyl, phenyl or substituted phenyl. In still another embodiment of compounds of Formula (I) and (II), D-E and F-G are both —C=C—, R¹, R² and R³ are independently hydrogen or methyl, W is —OR⁵ or —NR⁵R⁵ and each R⁵ is independently, hydrogen, methyl, ethyl or isopropyl, A is (C2-C3) alkylene or —CH₂—O—CH₂—, X is —CH₂—O— or —CH₂—, Y is methyl, phenyl or substituted phenyl. In still another embodiment of compounds of Formula (I) and (II), D-E and F-G are both cis —C=C—, R¹, R² and R³ are independently hydrogen or methyl, W is —OR⁵ or —NR⁵R⁵ and each R⁵ is independently, hydrogen, methyl, ethyl or isopropyl, A is (C2-C3) alkylene or —CH₂—O—CH₂—, X is —CH₂—O— or —CH₂—, Y is methyl, phenyl or substituted phenyl. In still another embodiment of compounds of Formula (I) and (II), D-E is cis —C=C-and F-G is trans —C=C—, R¹, R² and R³ are independently hydrogen or methyl, W is —OR⁵ or —NR⁵R⁵ and each R⁵ is independently, hydrogen, methyl, ethyl or isopropyl, A is (C2-C3) alkylene or —CH₂—O—CH₂—, X is —CH₂—O— or —CH₂—, Y is methyl, phenyl or substituted phenyl. In still another embodiment of compounds of Formula (I) and (II), D-E and F-G are both —C≡C—, R¹, R² and R³ are independently are independently hydrogen or methyl, W is —OR⁵ or —NR⁵R⁵ and each R⁵ is independently, hydrogen, methyl, ethyl or isopropyl, A is (C2-C3) alkylene or —CH₂—O—CH₂—, X is —CH₂—O— or —CH₂—, Y is methyl, phenyl or substituted phenyl.

In yet another embodiment, the present invention provides compounds of structural Formulae

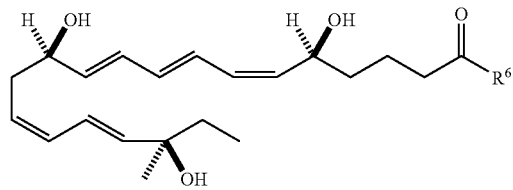
III

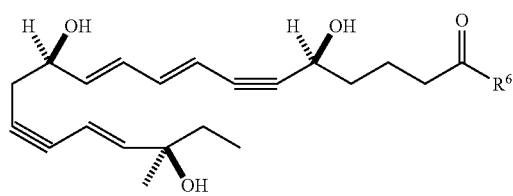
IV

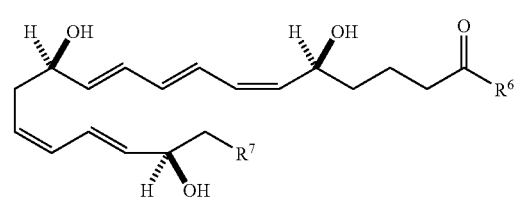
V

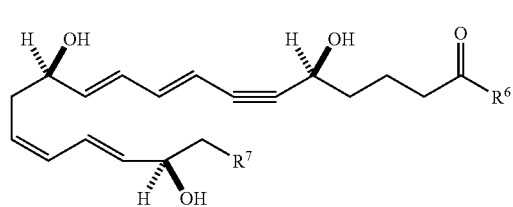
VI

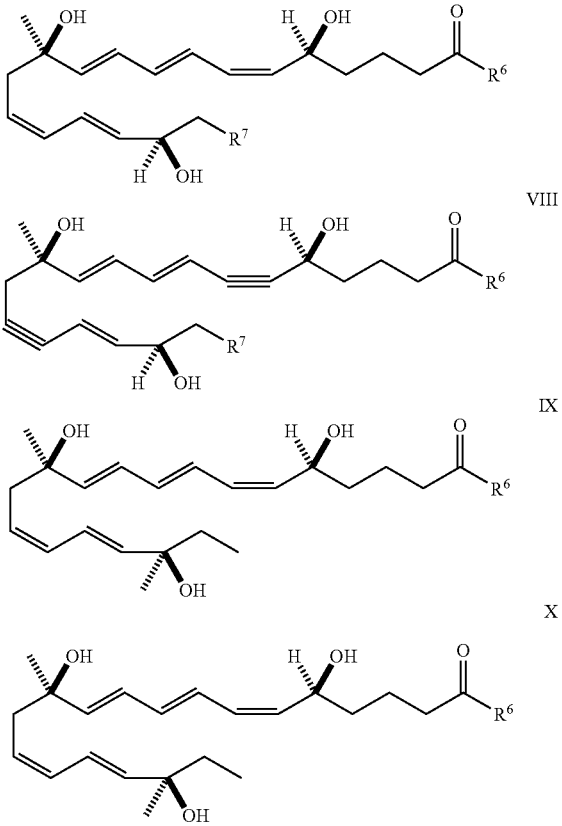

(III)-(X) and pharmaceutically acceptable salts, hydrates and solvates thereof, wherein R⁶ is —OH, —OCH₃, —OCH(CH₃)₂ or —NHCH₂CH₃ and R⁷ is

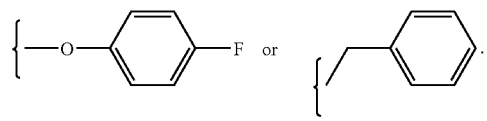

Detectable labels, as used herein, include, but are not limited to, fluorescence, phosphorescence, luminescence, radioactive or biospecific affinity capture labels. A radioactive label may an inherent part of a compound of the invention or may be attached either covalently or non-covalently to a compound of the invention. Similarly, fluorescent, phosphorescent, luminescent labels may also be attached either covalently or non-covalently to a compound of the invention. Fluorescent, phosphorescence, luminescence and radioactive labels are usually detected directly through instrumental measurements while biospecific affinity labels typically require reaction with another agent for detection (e.g., biotin is typically reacted with avidin for detection, IgG may be reacted with protein A or G for detection).

Detectable labels are either commercially available (e.g., Molecular Probes, Eugene, Oreg.) or may be readily synthesized by conventional methods. Further, labels may be attached covalently or non-covalently to compounds of the invention by methods well-known to the skilled artisan. Detectable labels may also be attached to compounds of the invention through a linking group. For example, a linking group may be a rigid polyunsaturated alkyl or an aryl, biaryl, heteroaryl etc., a flexible peptide such as Gly-Gly-Gly or a flexible saturated alkanyl or heteroalkanyl. Hydrophilic linking groups include, for example, polyalcohols or polyethers such as polyalkyleneglycols. Hydrophobic linking groups include, for example, alkyls or aryls. Choosing an appropriate linking group is well within the purview of those of skill in the art.

Typically, the compounds of the invention will be tested in biological assays (both in vitro and in vivo) well-known to those of skill in the art. Active compounds preferably have an $IC_{50}$, which is greater then 1 µM. Methods for determining $IC_{50}$ measurements in standard biological assays (both in vitro and in vivo) are well known to the skilled artisan. Preferably, in vivo biological activity is defined by physiological assays of anti-inflammatory activity known to skilled artisans, such as the murine dorsal air pouch assay and transepithelial cell migration [15].

Methods for Synthesis of Compounds of the Invention

Compounds of the invention can be prepared according to the generalized strategy illustrated in Scheme 1, where $R^P$ represents a hydroxyl protecting group.

-continued

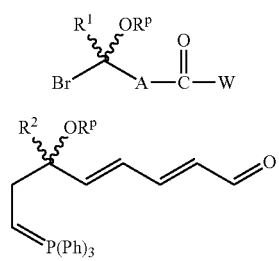

Generic Fragment A2

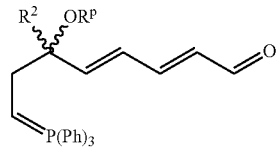

Generic Fragment B1

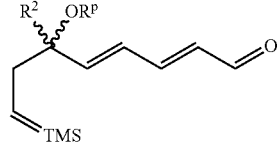

Generic Fragment B2

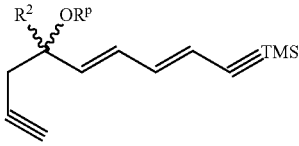

Generic Fragment B3

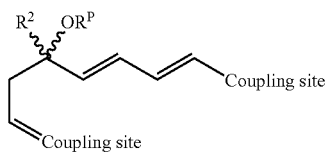

Generic Fragment B

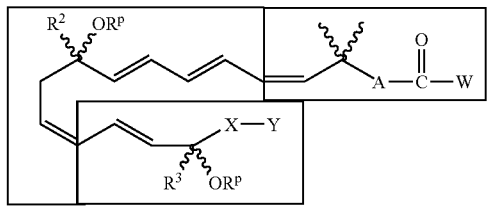

Generic Fragment A

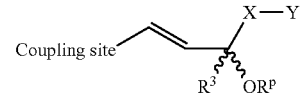

Generic Fragment C

Three major sets of generic fragments (A, B and C) have specific coupling sites shown below:

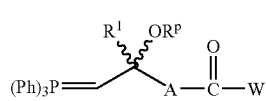

Generic Fragment A1

-continued

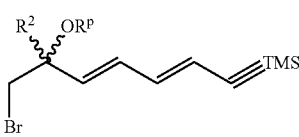

Generic Fragment B4

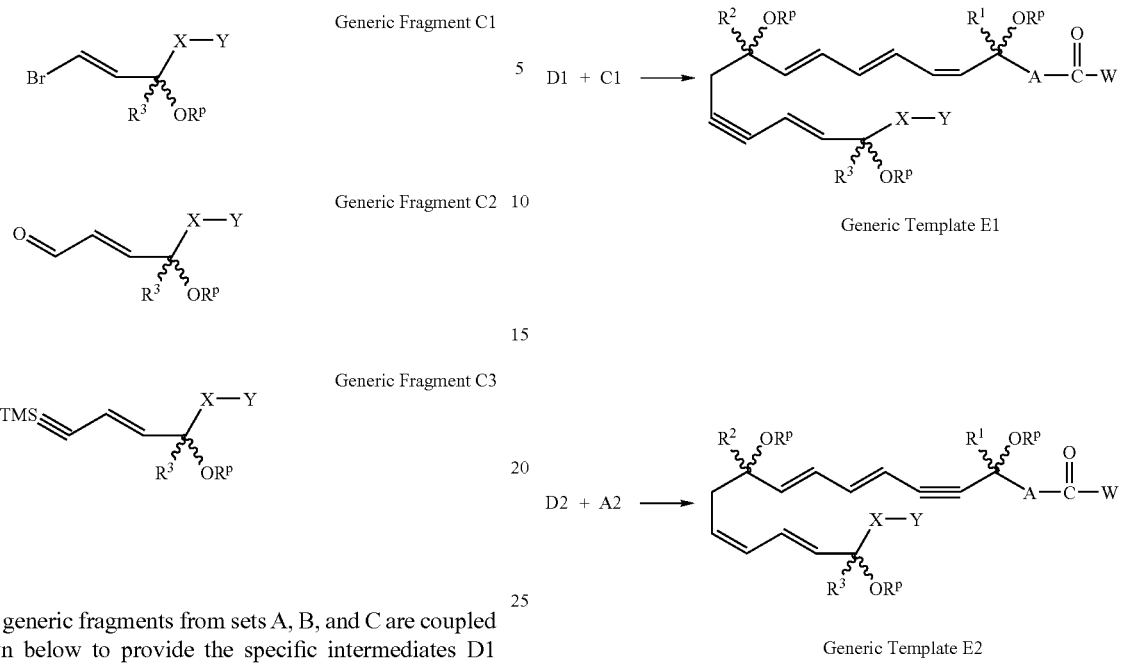

Generic Fragment C1

Generic Fragment C2

Generic Fragment C3

Specific generic fragments from sets A, B, and C are coupled as shown below to provide the specific intermediates D1 through D3. The illustrated strategy may be used to provide a preferred cis double bond or the acetylenic equivalent at the backbone positions exemplified below:

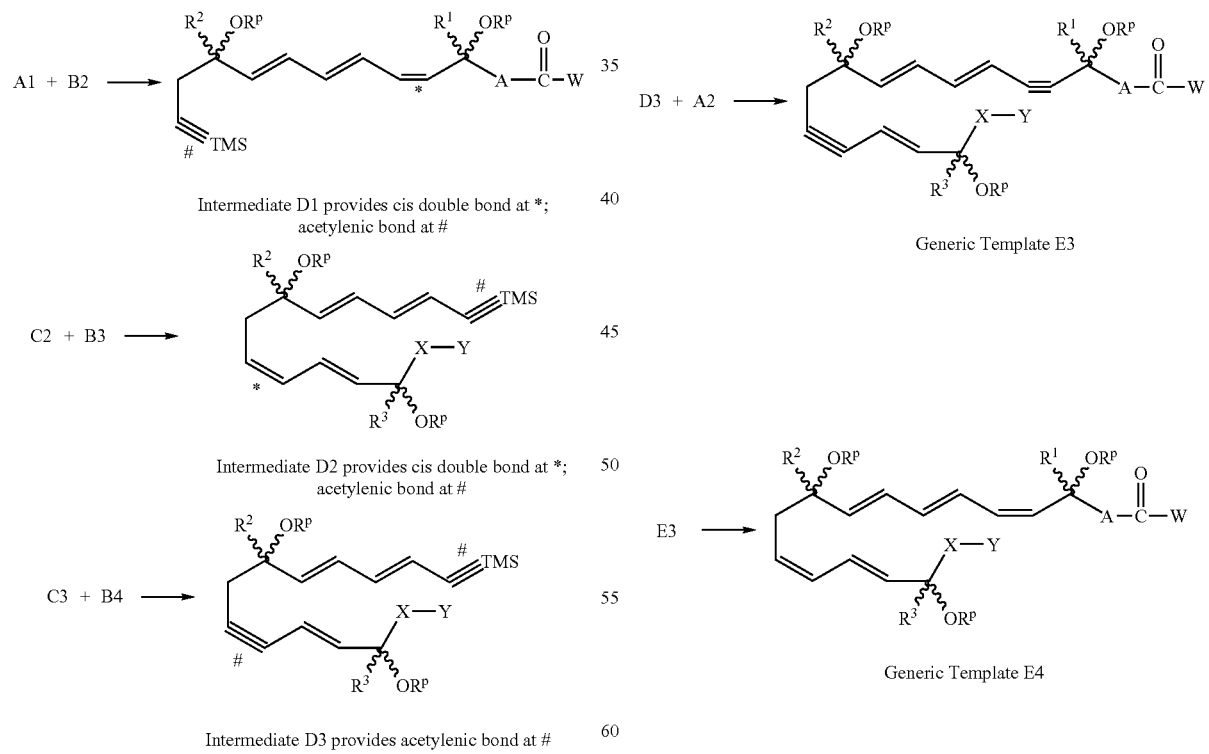

Intermediates D1 through D3 may be assembled into generic templates E1 through E3 as shown below. Template E3 can be converted to E4 by catalytic Lindlar hydrogenation to provide a cis alkene.

Exemplary syntheses of generic fragments of Set C provides hydroxyl-protected products C1' through C3' as illustrated below.

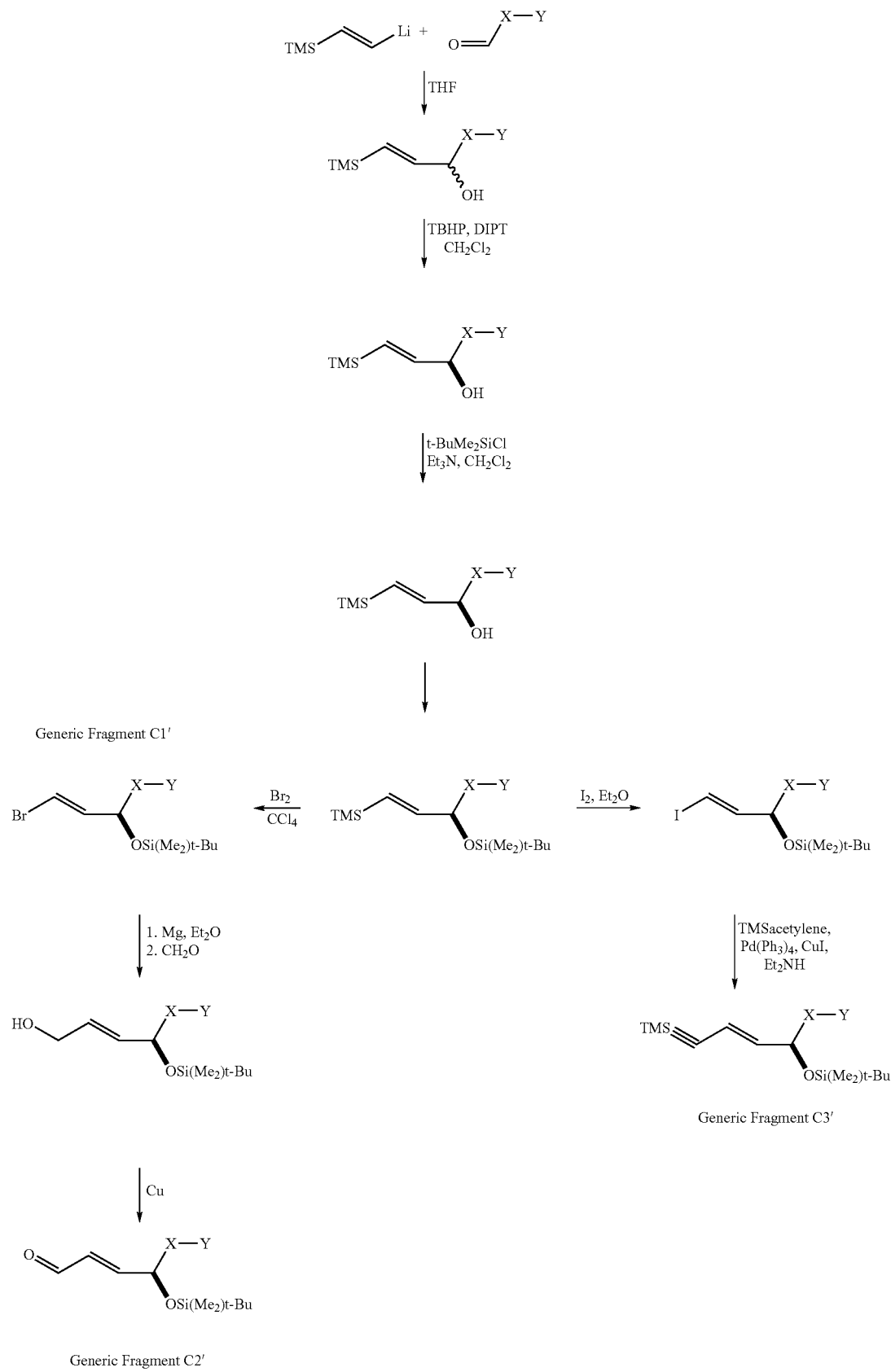

The hydroxyl-protected generic fragments can be protected by various protecting groups, which are well known to the skilled artisan [17].

The Schemes below illustrate specific routes to make preferred compounds. Other compounds of the invention can be made by combined routes derived from literature syntheses of eicosanoids and related PUFA analogues and derivatives by standard chemical methodologies [18-21].

potassium t-butoxide to produce intermediate 3. The protected compound 3 is desilyated, then reacted with vinyl bromide 4 using catalytic amounts of Pd(PPh$_3$)$_4$ and CuI to generate the hydroxyl-protected product which is deprotected by 10 equivalents of HF-pyr, THF, (0-25° C., 4 hr) followed by exposure to 3.0 equiv. of Et$_3$N, MeOH (25° C.15 min.). After deprotection, the final product 5 can be ,

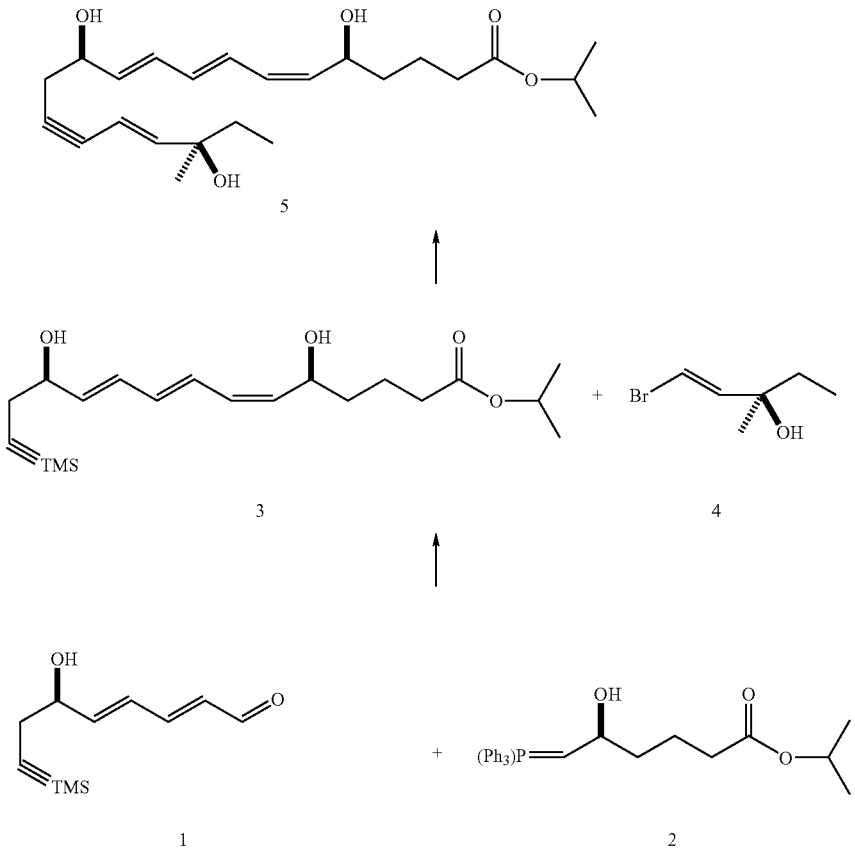

In Scheme 2, aldehyde 2 undergoes Wittig condensation with triphenylphosphonium bromide 1 in the presence of purified by reverse phase high pressure liquid chromatography ("RP-HPLC") [22].

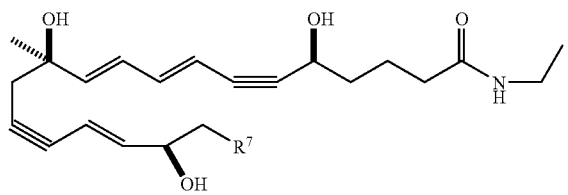

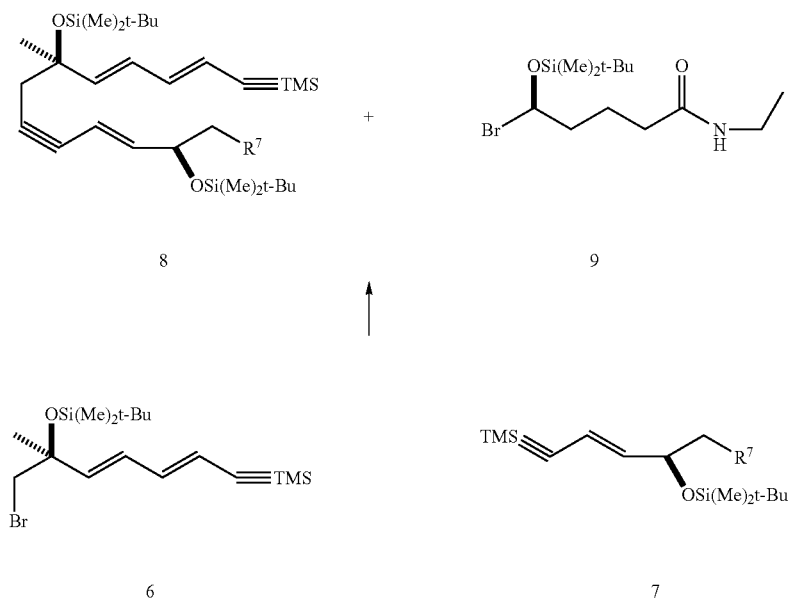

In Scheme 3, fluorophenoxy compound 6 is desilyated and then coupled with silyated triene 7. Self-condensation of 7 is minimized by sub-stoichiometric titration of reactive 6 with sequential addition of 0.1 equiv. of compound 7 until the reaction is complete. Protected compound 8 is reacted with bromoalkyl compound 9 to generate the OH-protected product, which is deprotected and purified as in Scheme 2 to provide final product 10.

Other methods and synthetic routes for synthesizing the compounds of the invention other than those discussed above are known to the skilled artisan. For example, preferred synthetic routes, which may be used by those of skill in the art to synthesize compounds of the invention include those described in references [32] and [33].

Utilities

The present invention also provides methods for treating or preventing inflammation in a subject by administering an effective amount of a compound of the invention to the subject. In one embodiment, an effective amount of a trihydroxy eicosapentaenoic acid analogue of 5,12,18R-triHEPE is administered to a subject to treat or prevent inflammation. In another embodiment, an effective amount of a compound of formula (I is administered to a subject to treat or prevent inflammation. In yet another embodiment, an effective amount of a compound of formula (II) is administered to a subject to treat or prevent inflammation. In still another embodiment, an effective amount of a compound of formulae (III), (IV), (V), (VI), (VII), (VIII), (IX), or (X) is administered to is administered to a subject to treat or prevent inflammation.

Examples of inflammatory conditions, which may be treated or prevented by the current invention, include inflammation of the lungs, joints, eyes, nose, bowel, kidney, liver, skin, central nervous system, vascular system and heart. Particularly relevant examples of inflammatory conditions, which may be treated by the current invention, include inflammation due to the infiltration of leukocytes or other immune effector cells into affected tissue. Other relevant examples of inflammatory conditions which may be treated by the present invention include inflammation caused by infectious agents, including but not limited to, viruses, bacteria fungi and parasites.

Inflammatory lung conditions include asthma, adult respiratory distress syndrome, bronchitis, pulmonary inflammation, pulmonary fibrosis, and cystic fibrosis (which may additionally or alternatively involve the bowel or other tissue(s)). Inflammatory joint conditions include rheumatoid arthritis, rheumatoid spondylitis, osteoarthritis, gouty arthritis and other arthritic conditions. Inflammatory eye conditions include uveitis (including iritis), conjunctivitis, scleritis, and keratoconjunctivitis sicca. Inflammatory bowel conditions include Crohn's disease, ulcerative colitis and distal proctitis.

Inflammatory skin diseases include conditions associated with cell proliferation, such as psoriasis, eczema and dermatitis, (e.g., eczematous dermatitides, topic and seborrheic dermatitis, allergic or irritant contact dermatitis, eczema craquelee, photoallergic dermatitis, phototoxic dermatitis, phytophotodermatitis, radiation dermatitis, and stasis dermatitis). Other inflammatory skin diseases include, but are not limited to, ulcers and erosions resulting from trauma, burns, bullous disorders, or ischemia of the skin or mucous membranes, several forms of ichthyoses, epidermolysis bullosae, hypertrophic scars, keloids, cutaneous changes of intrinsic aging, photoaging; frictional blistering caused by mechanical shearing of the skin and cutaneous atrophy resulting from the topical use of corticosteroids. Additional, inflammatory skin conditions include inflammation of mucous membranes, such as cheilitis, chapped lips, nasal irritation, mucositis and vulvovaginitis.

Inflammatory disorders of the endocrine system include, but are not limited to, autoimmune thyroiditis (Hashimoto's disease), Type I diabetes, and acute and chronic inflammation of the adrenal cortex. Inflammatory conditions of the cardiovascular system include, but are not limited to, coronary infarct damage, peripheral vascular disease, myocarditis, vasculitis, restenosis and artherosclerosis.

Inflammatory condition of the kidney include, but are not limited to, glomerulonephritis, interstitial nephritis, acute renal failure secondary to acute nephritis, post-obstructive syndrome and tubular ischemia.

Inflammatory conditions of the liver include, but are not limited to, hepatitis (arising from viral infection, autoimmune responses, drug treatments, toxins, environmental agents, or as a secondary consequence of a primary disorder), biliary atresia, primary biliary cirrhosis and primary sclerosing cholangitis.

Inflammatory conditions of the central nervous system include, but are not limited to, multiple sclerosis and neurodegenerative diseases such as Alzheimer's Disease or dementia associated with HIV infection. Other inflammatory conditions include periodontal disease, tissue necrosis in chronic inflammation, endotoxin shock, smooth muscle proliferation disorders, tissue damage following ischemia reperfusion injury, and tissue rejection following transplant surgery.

It should be noted that the current invention may be used to treat or prevent any disease which has an inflammatory component, such as those diseases cited above. Further, the inflammatory conditions cited above are meant to be exemplary rather than exhaustive. Those skilled in the art would recognize that additional inflammatory conditions (e.g., systemic or local immune imbalance or dysfunction due to an injury, an insult, infection, inherited disorder, or an environmental intoxicant or perturbant to the subject's physiology) may be treated by the current invention.

The present invention also provides methods for treating or preventing arthritis, inflammatory bowel disease, uveitis, ocular inflammation, asthma, pulmonary inflammation, cystic fibrosis, psoriasis, arterial inflammation, cardiovascular diseases, multiple sclerosis, or neurodegenerative disease by administering an effective amount of a compound of the invention. More particularly, the present invention provides methods for treating or preventing arthritis, inflammatory bowel disease or uveitis, by administering an effective amount of a compound of the invention.

In another embodiment, the present invention provides pharmaceutical compositions comprising one or more trihydroxy eicosapentaenoic acid analogues and a pharmaceutically acceptable vehicle. In one particular embodiment, the present invention provides a pharmaceutical composition comprising a trihydroxy eicosapentaenoic acid analogue of 5,12,18R-triHEPE and a pharmaceutically acceptable vehicle. In yet another embodiment, the present invention provides pharmaceutical compositions comprising one or more compounds of formulae (I), (II), (III), (IV), (V), (VI), (VIII), (IX) and X, and a pharmaceutically acceptable vehicle.

Typically, a pharmaceutical composition comprises a compound of the invention and a pharmaceutically acceptable vehicle. As used herein, "pharmaceutically acceptable vehicle" includes any and all solvents, dispersion media, coatings, antibacterial and antifungal agents, isotonic and absorption delaying agents, and the like that are physiologically compatible. Examples of pharmaceutically acceptable vehicles include one or more of water, saline, phosphate buffered saline, dextrose, glycerol, ethanol and the like, as well as combinations thereof. In many cases, isotonic agents, for example, sugars, polyalcohols such as mannitol, sorbitol, or sodium chloride may be included in the pharmaceutical composition. Pharmaceutically acceptable vehicles may further comprise minor amounts of auxiliary substances such as wetting or emulsifying agents, preservatives or buffers, which enhance the shelf life or effectiveness of a compound of the invention.

Pharmaceutical formulations can be prepared according to any method known in the art for the manufacture of pharmaceuticals. Such formulations can contain sweetening agents, flavoring agents, coloring agents and preserving agents. Any formulation can be mixed with nontoxic pharmaceutically acceptable excipients which are suitable for manufacture.

Pharmaceutical formulations for oral administration can be formulated using pharmaceutically acceptable vehicles well known in the art in dosages suitable for oral administration. Such vehicles enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of one or more compounds of the invention with a solid excipient, optionally grinding a resulting mixture, and processing the mixture of granules, after adding suitable additional compounds, if desired, to obtain tablets or dragee cores. Suitable solid excipients are typically carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain one or more compounds of the invention mixed with a filler or binders such as lactose or starches, lubricants such as talc or magnesium stearate, and, optionally, stabilizers: In soft capsules, the compounds of the invention may be dissolved or suspended in suitable liquids, such as fatty oils, liquid paraffin, or liquid polyethylene glycol with or without stabilizers.

Aqueous suspensions contain one or more compounds of the invention mixed with excipients suitable for the manufacture of aqueous suspensions. Such excipients include a suspending agent, such as sodium carboxymethylcellulose, methylcellulose, hydroxypropylnethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending one or more compounds of the invention in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid. Injectable oil vehicles are also known [24]. Dispersible powders and granules of the invention compounds suitable for preparation of an aqueous suspension by the addition of water can be formulated by mixing one or more compounds of the invention with a dispersing, suspending and/or wetting agent, and optionally one or more preservatives. Suitable dispersing or wetting agents and suspending agents are exemplified by those disclosed above. Additional excipients, for example sweetening, flavoring and coloring agents, can also be present.

The pharmaceutical formulations of the invention can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

The pharmaceutical formulations of the invention can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, such as a solution of 1,3-butanediol. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

For ocular administration, the active compound(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713.; 5,352,456; 5,332,213; 5,336,168; 5,290,561; 5,254,346; 5,164,189; 5,163,899; 5,088,977; 5,087,240; 5,008,110; and 4,921,475.

The compounds of the invention can be administered parenterally, topically, orally, ocularly by local administration, such as by aerosol or transdermally. The methods of the invention provide for prophylactic and/or therapeutic treatments. The compounds as pharmaceutical formulations can be administered in a variety of unit dosage forms depending upon the condition or disease and the degree of psychosis, the general medical condition of each patient, the resulting preferred method of administration and the like. Details on techniques for formulation and administration are well described in the scientific and patent literature [23].

The compounds of the invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials include, but are not limited to, cocoa butter and polyethylene glycols.

The compounds of the invention can also be administered by in intranasal, intraocular, intravaginal and intrarectal routes including suppositories, insufflation, powders and aerosol formulations (for examples of steroid inhalants, see [25,26]). Formulations of the invention which are preferably administered by the topical route can be administered as applicator sticks, solutions, suspensions, gels, creams, ointments, pastes, jellies, paints, powders and aerosols. The compounds of the invention can also be delivered transdermally or via intradermal injection of compound-containing microspheres, which slowly release subcutaneously [27]. The compounds of the invention can also be delivered using biodegradable and injectable gel formulations [28]. The compounds of the invention can also be delivered orally by the use of microspheres [29]. Both transdermal and intradermal routes afford constant delivery for weeks or months.

In certain embodiments, it may be desirable to introduce one or more compounds and/or compositions of the invention into the central nervous system by any suitable route, including intraventricular, intrathecal and epidural injection.

Intraventricular injection may be facilitated by an intraventricular catheter, for example, attached to a reservoir, such as an Ommaya reservoir.

A compound and/or composition of the invention may also be administered directly to the lung by inhalation. For administration by inhalation, a compound and/or composition of the invention may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the invention directly to the lung.

Alternatively, a Dry Powder Inhaler ("DPI") device may be used to administer a compound and/or composition of the invention to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of a compound of the invention and a suitable powder base such as lactose or starch for these systems.

Another type of device that may be used to deliver a compound and/or of the invention to the lung is a liquid spray device supplied, for example, by Aradigm Corporation. Liquid spray systems use extremely small nozzle holes to aerosolize liquid drug formulations that may then be directly inhaled into the lung.

In one embodiment, a nebulizer is used to deliver a compound and/or composition of the invention to the lung. Nebulizers create aerosols from liquid drug formulations by using, for example, ultrasonic energy to form fine particles that may be readily inhaled (see e.g., Verschoyle et al., *British J. Cancer*, 1999, 80, Suppl. 2, 96, which is herein incorporated by reference). Examples of nebulizers include devices supplied by Sheffield/Systemic Pulmonary Delivery Ltd. (See, Armer et al, U.S. Pat. No. 5,954,047; van der Linden et al., U.S. Pat. No. 5,950,619; van der Linden et al., U.S. Pat. No. 5,970,974), Aventis and Batelle Pulmonary Therapeutics.

In another embodiment, an electrohydrodynamic ("EHD") aerosol device is used to deliver a compound and/or composition of the invention to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering this compound to the lung with an EHD aerosol device and such optimization is routinely performed by one of skill in the art. EHD aerosol devices may more efficiently deliver drugs to the lung than existing pulmonary delivery technologies.

The compounds of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use.

The formulations of the invention may be useful for parenteral administration, such as intravenous administration or administration into a body cavity or lumen of an organ. The formulations for administration will commonly comprise a solution of one or more compounds of the invention dissolved in a pharmaceutically acceptable vehicle, preferably an aqueous carrier. A variety of aqueous carriers can be used, e.g., buffered saline and the like. These solutions are sterile and generally free of undesirable matter. These formulations may be sterilized by conventional, well-known sterilization techniques. The formulations may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of invention compound(s) in these formulations can vary widely, and will be selected primarily based on fluid volumes, viscosities, body weight and the like in accordance with the particular mode of administration selected and the patient's needs.

In another embodiment, the compounds of the invention can be delivered by the use of liposomes which fuse with the cellular membrane or are internalized by active or passive endocytotic processes. By using liposomes, particularly where the liposome surface carries ligands specific for target cells, or are otherwise preferentially directed to a specific organ, one can focus the delivery of the invention compound(s) into specific target cells in vivo [30,31].

In one embodiment, the compounds of the invention can be incorporated into a shampoo or a body cleansing product, e.g., a soap, for cleansing of the scalp and/or body. The use of the compounds of the invention in a shampoo or soap product may be used to treat psoriasis, seborrheic dermatitis, pustular dermatosis and dandruff. Additionally, the compounds of the invention can be used in topical lotions to treat the above-mentioned diseases as well as sunburn, poison ivy, dermatitis, and to slow the growth of metastatic cancers. Alternatively, the compounds of the invention can be used to treat Alzheimer's disease, where it is known that the action of anti-inflammatory agents helps to reduce the long term effect(s) of plaquing. In an alternative embodiment, the compounds of the invention can be used in an aerosol or spray to treat airway inflammation, e.g., bronchitis, asthma, pneumonia, emphysema, cystic fibrosis and upper respiratory illnesses in general.

Supplementary active compounds can also be incorporated into the compositions. In certain embodiments, a compound of the invention is coformulated with and/or coadministered with one or more additional therapeutic agents (e.g., enzyme inhibitors) that are useful for treating disorders in which inflammation is detrimental. For example, a compound of the invention may be coformulated and/or coadministered with one or more additional anti-inflammatory compounds (e.g., COX2 antagonists) that bind other targets, e.g., receptors. Furthermore, one or more compounds of the invention may be used in combination with two or more of the foregoing therapeutic agents. Such combination therapies may advantageously utilize lower dosages of the administered therapeutic agents, thus avoiding possible toxicities or complications associated with the various monotherapies.

The pharmaceutical compositions of the invention may include a "therapeutically effective amount" or a "prophylactically effective amount" of a compound of the invention.

A "therapeutically effective amount" refers to an amount effective, at dosages and for periods of time necessary, to achieve the desired therapeutic result, e.g., a diminishment or prevention of inflammation symptomology or disease process. A therapeutically effective amount of the compound of the invention may vary according to factors such as the disease state, age, sex, and weight of the individual, and the ability of the anti-inflammatory to elicit a desired response in the individual. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result on the disease. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In general, a suitable daily dose of a compound of the invention will be that amount which is the lowest dose effective to produce the desired therapeutic or prophylactic effect. Dosage will vary depending on route of administration and will typically be lower for local (ocular, topical) rather than systemic dosing. An exemplary, non-limiting range for a therapeutically or prophylactically effective amount of a compound of the invention is 0.01 mcg-50 mg/kg, more preferably from 0.1 mcg-10 mg/kg, still more preferably from 1 mcg-1 mg/kg. In one embodiment, a compound of the invention is systemically dosed at about between about 5 mcg/kg/day to about 30 mcg/kg/day, more preferably between about 5 mcg/kg/day to about 15 mcg/kg/day, most preferably, about 11 mcg/kg/day. In another embodiment, a compound of the invention is ocularly dosed at between about 1 mcg/eye/day to about 1.5 mcg/eye/day.

It should be noted that dosage values may vary with the type and severity of the condition to be alleviated. It should also be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Those skilled in the art will know, or be able to ascertain, using no more than routine experimentation, many equivalents to the specific embodiments of the invention described herein. These and all other equivalents are intended to be encompassed by the following claims.

REFERENCES CITED

1. De Caterina, R., S. Endres, S. D. Kristensen, and E. B. Schmidt, editors. (1993). n-3 Fatty Acids and Vascular Disease. Springer-Verlag, London
2. Lands, W. E. M., editor. (1987). Proceedings of the AOCS Short Course on Polyunsaturated Fatty Acids and Eicosanoids. American Oil Chemists' Society, Champaign, Ill.
3. Iigo, M. et al. (1997) *Br. J. Cancer* 75:650
4. Billman, G. E. et al. (1999) *Circulation.* 99:2452
5. Simopoulous, A. P. et al. (1999). *J. Am. Coll. Nutr.* 18:487
6. Marchioloi, R. et al. (1999). *Lancet.* 354:447
7. Weissmann, G. (1991). *Sci. Am.* 264:84-90
8. Marcus, A. J. (1999). In Inflammation: Basic Principles and Clinical Correlates. J Gallin and R. Snyderman, editors. Lippincott Williams & Wilkins, Philadelphia. pp77-9
9. Claria, J., and C. N. Serhan. (1995). *Proc. Natl. Acad. Sci.* USA 92:9475
10. Serhan, C. N et al. (1995). *Biochemistry* 34:14609
11. Chiang, N. et al. (1999). *J. Clin. Invest.* 104:309
12. Chiang, N. et al. (1998) *J. Pharmacol. Exp. Ther.* 287:779
13. Xiao, G. et al. (1997). *Biochemistry* 36:1836
14. Clish, C. B et al (1999). *Proc. Natl. Acad. Sci.* USA 96:8247
15. Serhan, C. N. et al. (2000). *J. Exp. Med* 192:1197
16. Cronstein, B. et al. (1992). *Proc. Natl. Acad. Sci.* USA 89:9991
17. Hanson, J. R. (1999) "Protecting Groups in Organic Synthesis", Blackwell Science
18. Webber, S. E. et al. (1988) *Adv. Exp. Med. Biol.* 229:61
19. Radüchel, B. and Vorbrüggen, H. (1985) *Adv. Prost. Thromb. Leuko. Res.* 14:263
20. Kobayashi, Y. et al. (1990) *J. Org. Chem.* 55:5324
21. Nicolaou, K. C. et al. (1991). *Agnew Chem. Int. Ed. Engl.* 30:1100
22. Serhan, C. et al. (1990) *Meth. Enzymol.* 187:167
23. "Remington's Pharmaceutical Sciences", Maack Publishing Co, Easton Pa.
24. Minto, C. (1997). *J. Pharmacol. Exp. Ther.* 281:93
25. Rohatagi, S. (1995). *J. Clin. Pharmacol.* 35:1187
26. Tjwa, M. (1995). *Ann. Allergy Asthma Immunol.* 75:107
27. Rao, S. (1995). *J. Biomater Sci. Polym. Ed.* 7:623
28. Gao, Z. et al. (1995) *Pharm. Res.* 12:857
29. Eyles, J. et al. (1997). *J. Pharm. Pharmacol.* 49:669
30. Al-Muhammed, J. et al. (1996). *J. Microencapsul.* 13:293
31. Ostro, M. and Cullis, P. (1989) *Am. J. Hosp. Pharm.* 46:1576
32. Shimazaki et al., (1993) *Prostaglandins* 45:335
33. Kobayashi et al., (1987) *Tetrahedron Lett.* 45: 5849

All publications and references cited herein, including those in the background section, are expressly incorporated herein by reference in their entirety.

What is claimed is:

1. A compound of structural formula (I):

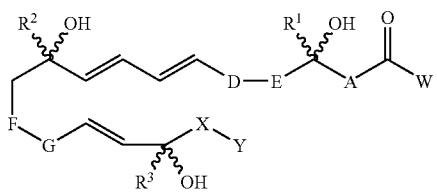

or a pharmaceutically acceptable salt thereof, wherein:

D-E and F-G are independently a cis or trans —C═C— or a —C≡C—;

$R^1$, $R^2$ and $R^3$ are independently selected from the group consisting of hydrogen, (C1-C4) alkyl, (C1-C4) alkoxy, —$CH_2R^4$, —$CHR^4R^4$ and —$CR^4R^4R^4$;

each $R^4$ is independently selected from —CN, —$NO_2$ and halogen;

W is selected from —$R^5$, —$OR^5$, —$SR^5$ and —$NR^5R^5$;

each $R^5$ is independently selected from hydrogen, (C1-C6) alkyl optionally substituted with one or more of the same or different R groups, (C5-C14) aryl optionally substituted with one or more of the same or different R groups, phenyl optionally substituted with one or more of the same or different R groups, (C6-C16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups, and a detectable label;

A is selected from (C1-C6) alkylene optionally substituted with 1, 2, 3, 4, 5 or 6 of the same or different halogen atoms, —$(CH_2)_m$—O—$CH_2$— and —$(CH_2)_m$—S—$CH_2$—, where m is an integer from 0 to 4;

X is selected from —$(CH2)_n$— and —$(CH2)_n$—O—, where n is an integer from 0 to 6;

Y is selected from hydrogen, (C1-C6) alkyl optionally substituted with one or more of the same or different R groups, (C5-C14) aryl optionally substituted with one or more of the same or different R groups, phenyl, optionally substituted with one or more of the same or different R groups, (C6-C16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups and a detectable label molecule;

each R is independently selected from an electronegative group, ═O, —$OR^a$, (C1-C3) haloalkyloxy, ═S, —$SR^a$, ═$NR^a$, ═$NONR^a$, —$NR^cR^c$, halogen, —$CF_3$, —CN, —NC, —OCN, —SCN, —NO, —$NO_2$, ═$N_2$, —$N_3$, —$S(O)R^a$, —$S(O)_2R^a$, —$S(O)2OR^a$, —$S(O)_2NR^cR^c$, —$OS(O)R^a$, —$OS(O)_2R^a$, —$OS(O)_2OR^a$, —$OS(O)_2NR^cR^c$, —$C(O)R^a$, —$C(O)OR^a$, —$C(O)NR^cR^c$, —$C(NH)NR^cR^c$, —$OC(O)R^a$, —$OC(O)OR^a$, —$OC(O)NR^cR^c$, —$OC(NH)NR^cR^c$, —$NHC(O)R^a$, —$NHC(O)OR^a$, —$NHC(O)NR^cR^c$ and —$NHC(NH)NR^cR^c$;

each $R^a$ is independently selected from hydrogen and (C1-C4) alkyl; and each $R^c$ is independently an $R^a$ or, alternatively, $R^cR^c$ taken together with the nitrogen atom to which it is bonded forms a 5 or 6 membered ring, with the proviso that when X-Y is —$CH_2CH_3$, then at least one of $R^1$, $R^2$ or $R^3$ is other than hydrogen.

2. The compound of claim 1 according to structural formula (II):

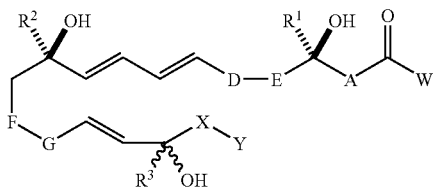

or a pharmaceutically acceptable salt thereof, wherein D-E and F-G, $R^1$, $R^2$, $R^3$, A, W, X and Y are as previously defined for claim 1, with the proviso that when X-Y is $CH_2CH_3$, then at least one of $R^1$, $R^2$ or $R^3$ is other than hydrogen.

3. The compound of claim 2 in which Y is phenyl optionally substituted with one or more of the same or different R groups, wherein each R is independently selected from an electronegative group, ═O, —$OR^a$, (C1-C3) haloalkyloxy, ═S, —$SR^a$, ═$NR^a$, ═$NONR^a$, —$NR^cR^c$, halogen, —$CF_3$, —CN, —NC, —OCN, —SCN, —NO, —$NO_2$, ═$N_2$, —$N_3$, —$S(O)R^a$, —$S(O)_2R^a$, —$S(O)_2OR^a$, —$S(O)_2NR^cR^c$, —$OS(O)R^a$, —$OS(O)_2R^a$, —$OS(O)_2OR^a$, —$OS(O)_2NR^cR^c$, —$C(O)R^a$, —$C(O)OR^a$, —$C(O)NR^cR^c$, —$C(NH)NR^cR^c$, —$OC(O)R^a$, —$OC(O)OR^a$, —$OC(O)NR^cR^c$, —$OC(NH)NR^cR^c$, —$NHC(O)R^a$, —$NHC(O)OR^a$, —$NHC(O)NR^cR^c$ and —$NHC(NH)NR^cR^c$.

4. The compound of claim 2 in which the hydroxyl group attached to the same carbon atom as the $R^3$ substituent is in the R configuration.

5. The compound of claim 2 in which:

W is —$OR^a$ or —$NHR^a$, where $R^a$ is as defined in claim 1;

A is —$(CH_2)_2$—, —$(CH_2)_3$— or —$CH_2OCH_2$—;

D-E and F-G are each independently a cis —C═C—;

$R^1$, $R^2$ and $R^3$ are independently, H or methyl;

n is 0 or 1; and

Y is (C1-C6) alkyl optionally substituted with from one to three of the same or different $R^d$ groups or phenyl optionally substituted with from one to three of the same or different $R^d$ groups, where each $R^d$ is independently selected from —$NO_2$, —CN, halogen, methyl and halogen-substituted methyl, with the proviso that if Y is phenyl or substituted phenyl, then $R^3$ is H.

6. The compound of claim 2 in which A is —$(CH_2)_2$—, —$(CH_2)_3$—, or —$CH_2OCH_2$—.

7. The compound of claim 2 which is selected from structural formulae (III-X):

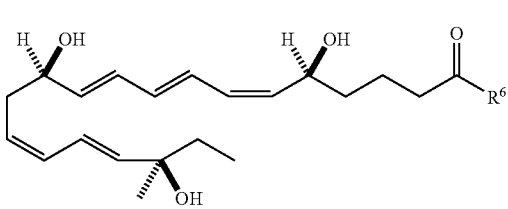

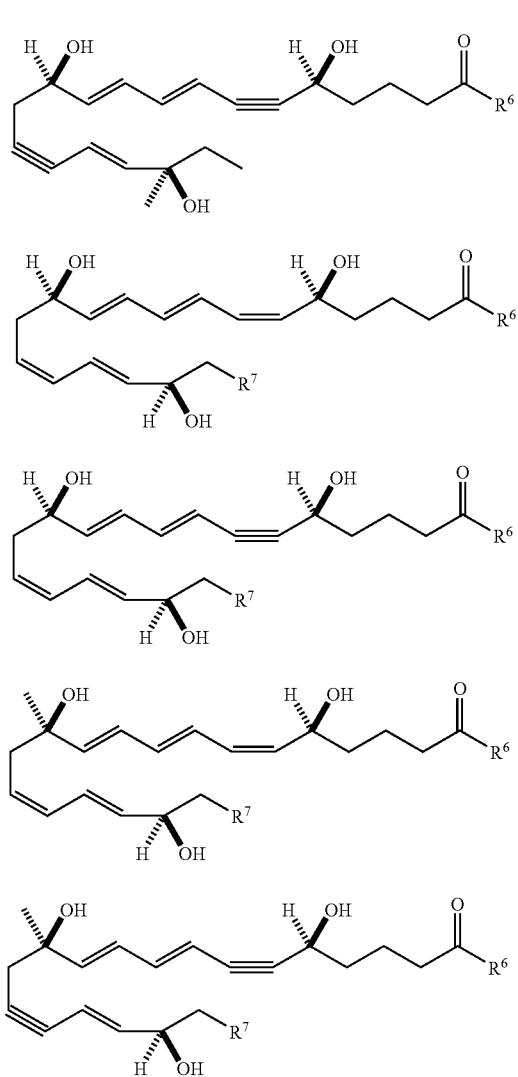

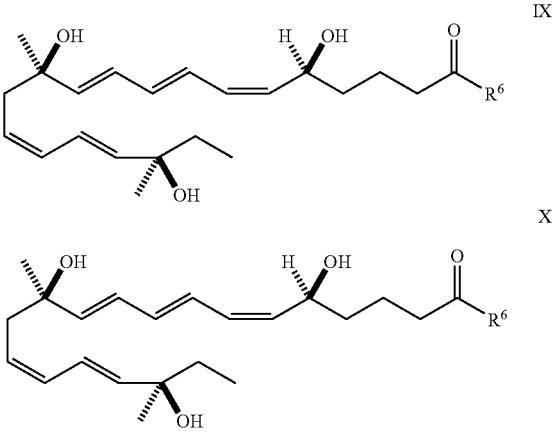

or a pharmaceutically acceptable salt thereof, wherein $R^6$ is —OH, —OCH$_3$, —OCH(CH$_3$)$_2$ or —NHCH$_2$CH$_3$ and $R^7$ is

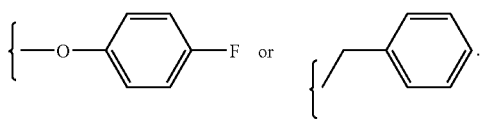

.

8. A pharmaceutical composition comprising a compound according to any one of claims 1-7 and a pharmaceutically acceptable vehicle.

9. A method for treating or preventing inflammation in a subject, comprising administering to the subject an effective amount of a compound according to any one of claims 1-7.

* * * * *

UNITED STATES PATENT AND TRADEMARK OFFICE
CERTIFICATE OF CORRECTION

PATENT NO.       : 7,378,444 B2                                          Page 1 of 1
APPLICATION NO.  : 10/460913
DATED            : May 27, 2008
INVENTOR(S)      : Goodman et al.

It is certified that error appears in the above-identified patent and that said Letters Patent is hereby corrected as shown below:

In claim 1, column 35, line 15, please replace "are independently" with --are each independently--;

In claim 1, column 35, lines 17-18, please delete "the group consisting of";

In claim 1, column 35, line 57, please replace "=$NR^3$," with --=$NR^a$,--;

In claim 1, column 35, line 59, please replace "-$S(O)2OR^a$," with -- -$S(O)_2OR^a$,--;

In claim 5, column 36, line 40, please replace "-$OR^a$" with -- -$OR^2$--;

In claim 5, column 36, line 44, please replace "independently, H" with --independently H--;

In claim 7, column 38, line 15, please replace " 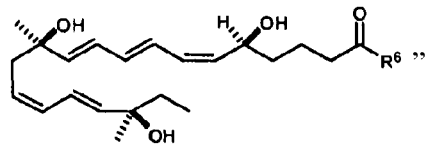 with -- 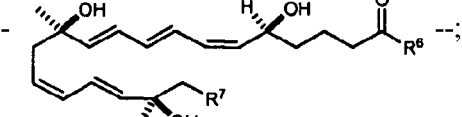 --;

In claim 9, column 38, line 40, please delete "or preventing" after "treating".

Signed and Sealed this

Nineteenth Day of August, 2008

JON W. DUDAS
*Director of the United States Patent and Trademark Office*